United States Patent
Kitten

(10) Patent No.: US 10,293,025 B2
(45) Date of Patent: May 21, 2019

(54) ORAL ADMINISTRATION COMPOSITIONS COMPRISING AN OB-FOLD PROTEIN VARIANT

(71) Applicant: AFFILOGIC, Nantes (FR)

(72) Inventor: Olivier Kitten, Nantes (FR)

(73) Assignee: AFFILOGIC, Nantes (FR)

( * ) Notice: Subject to any disclaimer, the term of this patent is extended or adjusted under 35 U.S.C. 154(b) by 0 days.

(21) Appl. No.: 15/521,398

(22) PCT Filed: Oct. 23, 2015

(86) PCT No.: PCT/EP2015/074644
§ 371 (c)(1),
(2) Date: Apr. 24, 2017

(87) PCT Pub. No.: WO2016/062874
PCT Pub. Date: Apr. 28, 2016

(65) Prior Publication Data
US 2018/0085427 A1 Mar. 29, 2018

(30) Foreign Application Priority Data

Oct. 24, 2014 (FR) ...................................... 14 60226

(51) Int. Cl.
| | | |
|---|---|---|
| *A61K 39/00* | (2006.01) | |
| *A61K 38/16* | (2006.01) | |
| *A61K 9/00* | (2006.01) | |
| *C07K 14/195* | (2006.01) | |
| *A61K 45/06* | (2006.01) | |

(52) U.S. Cl.
CPC .......... *A61K 38/164* (2013.01); *A61K 9/0053* (2013.01); *A61K 45/06* (2013.01); *C07K 14/195* (2013.01)

(58) Field of Classification Search
CPC .................................................... A61K 38/164
See application file for complete search history.

(56) References Cited

U.S. PATENT DOCUMENTS

2012/0100166 A1* 4/2012 Roschke .......... A61K 47/48415
424/185.1

FOREIGN PATENT DOCUMENTS

| WO | WO-2008/068637 A2 | 6/2008 |
| WO | WO-2012/150314 A1 | 11/2012 |
| WO | WO-2014/173899 A1 | 10/2014 |

OTHER PUBLICATIONS

Nimish Gera et al: "Highly Stable Binding Proteins Derived from the Hyperthermophilic Sso7d Scaffold", Journal of Molecular Biology, Academic Press, vol. 409, No. 4, 2011, pp. 601-616, XP028221838.
Muheem, A., et al., "A Review on the Strategies for Oral Delivery of Proteins and Peptides and Their Clinical Perspectives," Saudi Pharmaceutical Journal, vol. 24, pp. 413-428 (Jul. 2016) (published on-line Jun. 16, 2014).
Soltero, R.., et al., "The Oral Delivery of Protein and Peptide Drugs," Innovations in Pharmaceutical Technology, vol. 1, pp. 106-110 (Jan. 2001).

* cited by examiner

*Primary Examiner* — Albert M Navarro
(74) *Attorney, Agent, or Firm* — Polsinelli PC

(57) ABSTRACT

The invention relates to an oral administration composition containing an OB-fold protein variant, and to the method for preparing the same.

21 Claims, No Drawings
Specification includes a Sequence Listing.

SEQUENCE LISTING

<160> NUMBER OF SEQ ID NOS: 8

<210> SEQ ID NO 1
<211> LENGTH: 66
<212> TYPE: PRT
<213> ORGANISM: Sulfolobus acidocaldarius

<400> SEQUENCE: 1

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 2
<211> LENGTH: 64
<212> TYPE: PRT
<213> ORGANISM: Sulfolobus solfataricus

<400> SEQUENCE: 2

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 3
<211> LENGTH: 65
<212> TYPE: PRT
<213> ORGANISM: Sulfolobus acidocaldarius

<400> SEQUENCE: 3

Met Ala Lys Val Arg Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Met Asp Met Leu Ala Arg Ala Glu Lys Lys
    50                  55                  60

Lys
65

<210> SEQ ID NO 4
<211> LENGTH: 64
<212> TYPE: PRT
<213> ORGANISM: Sulfolobus shibatae

<400> SEQUENCE: 4

Met Val Thr Val Lys Phe Lys Tyr Lys Gly Glu Glu Lys Glu Val Asp
1               5                   10                  15

-continued

```
Thr Ser Lys Ile Lys Lys Val Trp Arg Val Gly Lys Met Ile Ser Phe
             20                  25                  30

Thr Tyr Asp Glu Gly Gly Gly Lys Thr Gly Arg Gly Ala Val Ser Glu
             35                  40                  45

Lys Asp Ala Pro Lys Glu Leu Leu Gln Met Leu Glu Lys Gln Lys Lys
 50                  55                  60

<210> SEQ ID NO 5
<211> LENGTH: 64
<212> TYPE: PRT
<213> ORGANISM: Sulfolobus shibatae

<400> SEQUENCE: 5

Met Ala Thr Val Lys Phe Lys Tyr Lys Gly Glu Glu Lys Gln Val Asp
 1               5                  10                  15

Ile Ser Lys Ile Lys Lys Val Trp Arg Val Gly Lys Met Ile Ser Phe
             20                  25                  30

Thr Tyr Asp Glu Gly Gly Gly Lys Thr Gly Arg Gly Ala Val Ser Glu
             35                  40                  45

Lys Asp Ala Pro Lys Glu Leu Leu Gln Met Leu Glu Lys Gln Lys Lys
 50                  55                  60

<210> SEQ ID NO 6
<211> LENGTH: 64
<212> TYPE: PRT
<213> ORGANISM: Sulfolobus sp.

<400> SEQUENCE: 6

Met Val Thr Val Lys Phe Lys Tyr Lys Gly Glu Glu Lys Glu Val Asp
 1               5                  10                  15

Ile Ser Lys Ile Lys Lys Val Trp Arg Val Gly Lys Met Ile Ser Phe
             20                  25                  30

Thr Tyr Asp Asp Asn Gly Lys Thr Gly Arg Gly Ala Val Ser Glu Lys
             35                  40                  45

Asp Ala Pro Lys Glu Leu Leu Gln Met Leu Glu Lys Ser Gly Lys Lys
 50                  55                  60

<210> SEQ ID NO 7
<211> LENGTH: 64
<212> TYPE: PRT
<213> ORGANISM: Sulfolobus islandicus

<400> SEQUENCE: 7

Met Val Thr Val Lys Phe Lys Tyr Lys Gly Glu Glu Lys Gln Val Asp
 1               5                  10                  15

Thr Ser Lys Ile Lys Lys Val Trp Arg Val Gly Lys Met Ile Ser Phe
             20                  25                  30

Thr Tyr Asp Glu Gly Gly Gly Lys Thr Gly Arg Gly Ala Val Ser Glu
             35                  40                  45

Lys Asp Ala Pro Lys Glu Leu Leu Gln Met Leu Glu Lys Gln Lys Lys
 50                  55                  60

<210> SEQ ID NO 8
<211> LENGTH: 60
<212> TYPE: PRT
<213> ORGANISM: Artificial
<220> FEATURE:
<223> OTHER INFORMATION: Consensus sequence
<220> FEATURE:
<221> NAME/KEY: VARIANT
<222> LOCATION: (2)..(2)
```

```
<223> OTHER INFORMATION: Xaa is V, A or T
<220> FEATURE:
<221> NAME/KEY: VARIANT
<222> LOCATION: (3)..(3)
<223> OTHER INFORMATION: Xaa is T or K
<220> FEATURE:
<221> NAME/KEY: VARIANT
<222> LOCATION: (5)..(5)
<223> OTHER INFORMATION: Xaa is R or K
<220> FEATURE:
<221> NAME/KEY: VARIANT
<222> LOCATION: (14)..(14)
<223> OTHER INFORMATION: Xaa is E or Q
<220> FEATURE:
<221> NAME/KEY: VARIANT
<222> LOCATION: (17)..(17)
<223> OTHER INFORMATION: Xaa is T or I
<220> FEATURE:
<221> NAME/KEY: VARIANT
<222> LOCATION: (30)..(30)
<223> OTHER INFORMATION: Xaa is A, V or I
<220> FEATURE:
<221> NAME/KEY: VARIANT
<222> LOCATION: (36)..(38)
<223> OTHER INFORMATION: Xaa Xaa Xaa is EGG or DN-
<220> FEATURE:
<221> NAME/KEY: VARIANT
<222> LOCATION: (56)..(56)
<223> OTHER INFORMATION: Xaa is M or L
<220> FEATURE:
<221> NAME/KEY: VARIANT
<222> LOCATION: (57)..(57)
<223> OTHER INFORMATION: Xaa is Q or D
<220> FEATURE:
<221> NAME/KEY: VARIANT
<222> LOCATION: (60)..(60)
<223> OTHER INFORMATION: Xaa represent A, ARAE, EKQKK, EKSGKK, ARAEREKK,
      ARAEKKK, ACAEREKK or ACAEKKK

<400> SEQUENCE: 8

Met Xaa Xaa Val Xaa Phe Lys Tyr Lys Gly Glu Glu Lys Xaa Val Asp
1               5                   10                  15

Xaa Ser Lys Ile Lys Lys Val Trp Arg Val Gly Lys Met Xaa Ser Phe
            20                  25                  30

Thr Tyr Asp Asp Asn Xaa Gly Lys Thr Gly Arg Gly Ala Val Ser Glu
        35                  40                  45

Lys Asp Ala Pro Lys Glu Leu Xaa Xaa Met Leu Xaa
    50                  55                  60
```

ORAL ADMINISTRATION COMPOSITIONS COMPRISING AN OB-FOLD PROTEIN VARIANT

RELATED APPLICATIONS

This application is a national stage application (under 35 U.S.C. § 371) of PCT/EP2015/074644, filed Oct. 23, 2015, which claims benefit of French application FR 1460226, filed Oct. 24, 2014.

The invention relates to the field of the preparation of oral compositions for therapeutic use, containing active ingredients which bind to targets of interest.

There are a certain number of gastrointestinal system diseases. In order to treat these diseases it is desirable to be able to have available compositions which act directly at the site of the disease.

To do this, it is possible to develop rectal compositions, but oral compositions are preferred by patients and enable better compliance to the treatment. Moreover, and even for treating systemic diseases (not localized in the gastrointestinal system), oral administration is preferred, as far as possible, to other modes of administration (and in particular injections), which can require the involvement of members of the care staff.

Whatever the disease, there is generally a target of therapeutic interest on which the medicaments are active. This may be a cell receptor, or a surface protein of a microorganism. Generally, it appears to be desirable to have compositions enabling the application of active ingredients which act on the targets of therapeutic interest directly on the site of action. However, some proteins, such as antibodies, are degraded when they pass through the stomach.

Application WO 2007/139397 describes the use of libraries of OB-fold proteins in which the OB domain is modified by introducing mutations into this domain for binding of the protein to its natural ligand.

Application WO 2008/068637 describes the use of a library based on the Sac7d protein for obtaining ligands which have an affinity for targets of interest. The method described in WO 2008/068637 comprises the generation of combinatorial libraries containing a plurality of DNA molecules all having the same sequence, except for the presence of certain random mutations leading to the production of variants of a wild-type protein, exhibiting mutations at certain amino acids of the binding site of this wild-type OB-fold protein. In particular, in the context of WO 2008/068637, the wild-type OB-fold protein is a Sac7d protein, into which mutations are introduced in order to generate a variability, in particular at amino acids chosen from K7, Y8, K9, K21, K22, W24, V26, M29, S31, T33, T40, R42, A44, S46, or on other amino acids, such as V26, G27, K28, M29, S31, R42, A44, S46, E47 and K48. These amino acids are based on the Sac7d sequence, as represented by SEQ ID No. 1.

Patent application WO 2012/150314 presents the portability of mutations from one protein of the Sac7d family to another protein of the same family. This portability amounts to creating a mutant of another protein of the Sac7d family from a mutant of one protein of said family, that it has been possible to obtain in particular by carrying out the process of WO 2008/068637.

The Sac7d family is defined as relating to the Sac7d family and corresponds to a family of 7 kDa DNA-binding proteins isolated from extremophilic bacteria. These proteins and this family are in particular described in WO 2008/068637. Thus, within the context of the present invention, a protein belongs to the Sac7d family when it has a sequence corresponding to the sequence SEQ ID No. 8. This family comprises in particular the Sac7d or Sac7e proteins derived from *Sulfolobus acidocaldarius*, the Sso7d protein derived from *Sulfolobus solfataricus*, the DBP 7 protein derived from *Sulfolobus tokodaii*, the Ssh7b protein derived from *Sulfolobus shibatae*, the Ssh7a protein derived from *Sulfolobus shibatae*, and the 7ss protein derived from *Sulfolobus solfataricus*.

The OB-fold proteins are known in the art. They are in particular described in the documents cited above, and also in Arcus (Curr Opin Struct Biol. 2002 December; 12(6): 794-801). OB-fold is in the form of a cylinder having five beta (β) sheets. Most OB-fold proteins use the same binding interface of their natural ligand, which may be an oligosaccharide, an oligonucleotide, a protein, a metal ion or a catalytic substrate. This binding interface comprises mainly the residues located in the beta sheets. Certain residues located in the loops may also be involved in the binding of an OB-fold protein with its natural ligand. Thus, applications WO 2007/139397 and WO 2008/068637 and the Arcus document (2002, op. cit.) describe the OB-fold-protein domains for binding with their natural ligand. Thus, document WO 2008/068637 describes precisely how to identify the binding domain of an OB-fold protein.

By superimposing several sequences and 3D structures of proteins having OB-fold domains, using the websites WU-Blast2 (http://www.ebi.ac.uk/blast2/index.html) (Lopez et al., 2003, Nucleic Acids Res 31, 3795-3798), T-COFFEE (http://www.ch.embnet.org/software/TCoffee.html) (Notredame et al., 2000, J Mol Biol 302, 205-217) and DALI lite (http://www.ebi.ac.uk/DaliLite/) (Holm and Park, 2000, Bioinformatics 16, 566-567), it is possible to identify the positions of the binding domains and in particular the amino acids which can be modified. Taking the sequence of Sac7d (SEQ ID No. 1) as reference, these are the residues V2, K3, K5, K7, Y8, K9, G10, E11, K13, E14, T17, K21, K22, W24, V26, G27, K28, M29, S31, T33, Y34, D36, N37, G38, K39, T40, R42, A44, S46, E47, K48, D49, A50 and P51.

Still with this Sac7d sequence as reference, the residues which can be deleted are: A59, R60, A61, E64 and/or K66.

The binding domains of other OB-fold proteins can be identified as described in WO 2008/068637. This application indicates that it is possible to perform a superimposition of 3D structures of OB-fold proteins or domains (10 domains were used in this application, including Sac7d), using the DALI website (http://www.ebi.ac.uk/dali/interactive.html) (Holm and Sander, 1998, Nucleic Acids Res 26, 316-319). Thus, it is easy to identify, for any OB-fold protein (or any OB-fold domain), the amino acids involved in the binding site and corresponding to the Sac7d amino acids mentioned above.

The teaching of WO 2008/068637 also indicates that amino acids can optionally be inserted into the loops of the OB-fold proteins, in particular the proteins of the Sac7d family; in particular, insertions of 1 to 15 amino acid residues can be made in loop 3 (as defined in FIGS. 1b and 2 of WO 2008/068637), for example in the region of residues 25 to 30 of Sac7d, preferably between residues 27 and 28, insertions of 1 to 15 amino acid residues can be made in loop 4 (as defined in FIGS. 1b and 2 of WO 2008/068637), for example in the region of residues 35-40 of Sac7d, preferably between residues 37 and 38, and insertions of 1 to 20 residues can be made in loop 1 (as defined in FIGS. 1b and 2 of WO 2008/068637), for example in the region of residues 7 to 12 of Sac7d, preferably between residues 9 and 10.

By extension, in the context of the present application, the term "OB-fold protein" comprises the natural OB-fold proteins, but also the domains which have an OB-fold that can be isolated from more complex proteins. These OB-fold domains are in particular described in greater detail in applications WO 2007/139397 and WO 2008/068637. This term also comprises the polypeptides that can be obtained by fusing, by genetic engineering, in the N- or C-terminal position, an OB-fold protein or a domain which has an OB-fold to a protein or a domain of interest, for example a tag allowing better purification.

The advantage of the method described in WO 2008/068637 is that it makes it possible to obtain variants of OB-fold proteins by screening combinatorial libraries containing or expressing a plurality of variants in which a certain number of amino acids have been "randomized", i.e. replaced with a random amino acid. The screening of these libraries makes it possible to identify variants of these proteins which bind specifically, generally with a strong affinity (application WO 2008/068637 in fact describes affinities of the order of one nanomolar), with a target of interest, other than the natural ligand of the wild-type protein from which the combinatorial library was generated.

The inventors have shown that the OB-fold proteins are sufficiently resistant to gastric degradation, and can remain in the intestine or cross the barrier of the intestine and thus be used in compositions that can be used orally for the treatment of various diseases, in particular localized in the intestine, or in other organs of the body, after passage through the systemic circulation. Use is preferably made of a variant of an OB-fold protein, which binds to a target of interest, said target of interest being involved in a pathological condition, in particular of the gastrointestinal system, or a systemic pathological condition (that is to say a pathological condition located in an organ other than the gastrointestinal system).

The present invention thus relates to a composition for oral administration comprising an OB-fold protein or a variant of a wild-type OB-fold protein, said variant having between 5 and 32 mutated residues in the interface of binding of said wild-type OB-fold protein to its natural ligand.

In one particular embodiment, said variant exhibits therapeutic activity. In particular, said variant binds specifically to a target of interest other than the target of said natural ligand. This variant can then have been identified by implementing a method as described in WO 2008/068637 or WO 2007/139397. In fact, the implementation of the methods described in these two patent applications generally makes it possible to identify variants of any OB-fold protein which binds to any target of interest. This composition also generally contains a pharmaceutically acceptable excipient that can be used for such an oral administration.

As seen above, said wild-type OB-fold protein also encompasses the OB-fold domains. Preferably, the variant used in the context of the present invention contains a maximum of 300 amino acids, preferably a maximum of 200 amino acids, preferably a maximum of 175 amino acids, more preferably a maximum of 150 amino acids, more preferably a maximum of 100 amino acids. In one particular embodiment, it contains a maximum of 80 or a maximum of 70 amino acids.

The number of mutated residues in said variant (relative to the wild-type protein) is between 5 and 32. In other embodiments, these variants preferably have at least 5, more preferably at least 8, even more preferably at least 10, but generally less than 32, more preferably less than 24, even more preferably less than 20 or less than 15 substituted amino acids compared with the wild-type OB-fold protein (or domain). It is preferred when 8, 9, 10, 11, 12, 13 or amino acids are mutated relative to the wild-type protein. These mutated amino acids are located in the site of binding of the OB-fold protein with its natural ligand. They are generally distributed over the whole of this binding domain. Given the structure of this binding domain, certain mutated residues are found in a (generally several, in particular two or three) beta sheet.

In one particular embodiment, these variants can also comprise amino acid insertions in loops linking the beta sheets of the OB-fold. Thus, between 1 and 15 amino acids can be introduced into loop 1 and/or into loop 4 and/or into loop 3 (the loops being numbered in the same way as in WO 2008/068637).

In one particular embodiment, said wild-type OB-fold protein is chosen from Sac7d or Sac7e derived from *Sulfolobus acidocaldarius*, Sso7d derived from *Sulfolobus solfataricus*, DBP 7 derived from *Sulfolobus tokodaii*, Ssh7b derived from *Sulfolobus shibatae*, Ssh7a derived from *Sulfolobus shibatae*, and p7ss derived from *Sulfolobus solfataricus*.

It is therefore the protein with which the variant used in the oral administration composition of the present invention is compared.

The various sequences of the Sac7d, Sso7d, Sac7e, Ssh7b, Ssh7a, DBP7 and Sis7 proteins are represented by SEQ ID No. 1 to SEQ ID No. 7 respectively.

A variant of a protein of this Sac7d family is called a nanofitin. The invention is thus preferentially implemented on variants of the proteins represented by SEQ ID No. 1 to SEQ ID No. 7, in particular on variants of Sac7d.

In the case of a liquid composition, the concentration of the variant in the composition according to the present invention is generally greater than 10 ng/ml and less than 600 mg/ml. It is thus generally less than 500 mg/ml, preferably less than 250 mg/ml, preferably less than 100 mg/ml, or than 50 mg/ml, or even less than 10 mg/ml. It is generally greater than 10 ng/ml, preferably greater than 50 ng/ml, preferably greater than 100 ng/ml.

The concentration is adjusted to the dose that it is desired to administer to the patient for an intake of between 5 and 20 ml.

For a solid composition, the dose is adjusted according to the number of tablets (or lozenges or the like) that the patient will take in order to obtain the dose that is effective from a therapeutic point of view.

Generally, a very variable amount (which will depend in particular on the nature of the disease, on the antigen targeted, optionally on the affinity of the variant of the OB-fold protein against this antigen, on the weight of the patient, on the use in combination or not with other medicaments for the pathological condition) is administered to the patient. The range will thus generally go from 10 mg/kg up to 200 mg/kg, or even 400 mg/kg of the OB-fold protein variant in one or more intakes. However, and as stated above, these limit values are only indications, and it is possible to prepare compositions for administering more or less product.

The variant present in the composition according to the invention binds specifically to a target of interest. In fact, it may have been selected, by means of a method such as described in WO 2008/068637 or WO 2007/139397, for its binding specificity with this target of interest. Moreover, the methods described in these patent applications make it possible to obtain affinities of the order of one micromolar (WO 2007/139397) or of one nanomolar (WO 2008/068637).

The targets of interest are chosen according to the disease that it is desired to treat. Mention may thus be made of any antigen, antibody, cell protein, circulating protein, or peptides. It is also possible to target an active ingredient of a medicament, or a particular nucleic acid. It is in particular envisioned that the target of interest is an interleukin, a cytokine, a cytokine or interleukin receptor, a protein encoded by an oncogene, a surface protein of a microorganism, or a microorganism lipopolysaccharide.

The composition according to the invention may be in any form known in the art. In particular, it is in the form of gel capsules, tablets (film-coated or not film-coated), pills or lozenges. In another embodiment, it is in the form of a liquid composition, such as a syrup. It can also be in the solid form.

In the case where the composition is in a solid form, use may be made of any excipient known in the art, such as talc (E553b), microcrystalline cellulose, lactose, starch (in particular corn starch), magnesium stearate (E572), stearic acid (E570) or microcrystalline cellulose. When the composition is in the form of a film-coated tablet, said film coating can be formed from any substance known in the art, such as hypromellose (E464), ethylcellulose, macrogol, talc (E553b), titanium dioxide (E171) or iron oxide (E172).

The compositions can also be slow release. Such controlled- or slow-release formulations are described, in particular, in WO 2011/077239. Thus, these compositions can include matrices in which the OB-fold proteins (natural or variants) are present, optionally with other ingredients. These matrices can be such that they allow immediate release of a part of the OB-fold proteins, followed by slow release of another part of these proteins.

In the oral compositions which are in solid form, the proteins can be lyophilized or integrated into matrices as described in WO 98/043615.

However, it should be noted that the examples clearly show that the OB-fold protein variants, in particular when the OB-fold protein is of the Sac7d family (SEQ ID No. 1 to SEQ ID No. 7), are resistant to gastric degradation and can thus exert their effects in the intestine, or even in the systemic circulation. It is thus clear that, even though the elements of the oral administration composition can make it possible to improve the protection of these proteins, this is just a plus, not an element essential to the production of the technical effect.

When the compositions are in liquid form, the proteins are generally present directly in the solution.

Use is generally made of PBS (phosphate buffered saline, a physiological solute containing sodium chloride, disodium phosphate, monopotassium phosphate and a small amount of potassium chloride), TBS (tris-buffered saline), citrate buffer (produced in particular with 100 mM monosodium citrate) or HEPES (4-(2-hydroxyethyl)-1-piperazineethanesulfonic acid, a zwitterionic organic compound which is a buffer with good stability at physiological pH).

Other than the citrate buffer for which the pH is adjusted to between 4 and 6, the buffers are preferentially at pH 7.4.

However, it is possible to use other types of buffers for preparing the oral liquid compositions.

Of course, it is preferable for these buffers to be prepared under conditions which allow administration to patients (traceability, good manufacturing practices, etc.).

The variants of the OB-fold proteins, used in the composition according to the invention, can be produced by solid-phase chemical synthesis or by genetic recombination.

The chemical synthesis can be carried out, for example, with an Applied Biosystems automatic peptide synthesizer, mod. 433A., or by Fmoc chemistry which uses the fluorenylmethyloxycarbonyl group for temporary protection of the α-amino function of the amino acids.

However, it is preferred to produce the variants that can be used in the context of the invention by genetic engineering, in particular by integrating a nucleic acid sequence encoding said polypeptide into an expression vector. This expression vector is then introduced into a host cell (bacteria such as *Escherichia coli* are particularly suitable), which is cultured under culture conditions allowing the synthesis of the polypeptide (use may in particular be made of inducible promoters upstream of the polypeptide in the expression vector). The polypeptide synthesized is then recovered. Molecules of any type can then be grafted in the N- or C-terminal position of the polypeptide.

Those skilled in the art are aware of the methods for producing polypeptides, which are in particular described in the book by Sambrook, Fritsch and Maniatis, Molecular Cloning, A Laboratory Manual, $2^{nd}$ edition.

The composition according to the invention can contain variants of the OB-fold protein, alone or with other active ingredients. Thus, the composition can also contain at least one agent chosen from antibacterial, antiparasitic, antifungal, anti-inflammatory, antipruritic, anesthetic, antiviral, keratolytic and free-radical-scavenger agents.

This composition can also have a pH regulator, in particular for enabling the pH to be regulated to around pH=7.

The variants of the OB-fold protein can also be fused with an active protein, or any other compound, in particular in order to increase their half-life time.

The composition according to the invention can also be used in a diagnostic method. Thus, in one particular embodiment, the variant of the OB-fold protein is coupled to a detection or contrast agent, a tracer or a metal. This makes it possible in particular to follow this detection agent (contrast agent, tracer, metal) and to determine the organs to which the variant of the OB-fold protein binds (thereby indicating the presence of the target of interest). The invention therefore relates to a method for detecting the presence of a specific antigen in an organ, in particular in the gastrointestinal system, comprising the step of administering an oral composition as described above, said composition comprising an OB-fold protein variant which binds to said antigen, and which is coupled to a detectable tracer (in particular the detection of the radiation emissions emitted by the tracer, or a metal, or a contrast agent). This method can also comprise the step of detecting the presence of the tracer in the human body, and of localizing the organ in which this tracer is detected, making it possible to conclude that the antigen is present in the organ where this tracer is detected. This conclusion with regard to the presence of the antigen in an organ is key for reaching a conclusion in this diagnostic method, since it makes it possible to reach a conclusion with regard to the existence of a particular pathological condition, in particular if the antigen is a marker for this pathological condition. The most common tracers are isotopes (with a half-life of less than two hours), such as fluorine 18 ($^{18}$F) or other radioelements such as $^{15}$O, $^{13}$N and $^{11}$C.

The invention also relates to a process for preparing an oral administration composition, comprising the step of mixing a variant of a wild-type OB-fold protein with a pharmaceutically acceptable oral administration excipient.

The invention also relates to an oral administration composition, according to the invention, containing a variant of a wild-type OB-fold protein, said variant having between 5 and 32 mutated residues in the interface of binding of said wild-type OB-fold protein to its natural ligand, as a medicament. In this particular case, said variant binds specifically to a target of interest, which is a therapeutic target.

The invention also relates to an oral administration composition according to the invention for treating a systemic disease or disorder or more specifically a gastrointestinal system disease or disorder. In this embodiment, the OB-fold protein variant used targets (binds to) an etiological factor of the envisioned disease or a therapeutic target associated with this disease.

A gastrointestinal system disease is a disease in particular chosen from amibiasis, colon and rectal cancers, stomach and duodenal cancers, esophageal cancers, inflammatory bowel disease (IBF), pancreatic cancer, cholera, hepatitis and cirrhosis of the liver (in particular hepatic cirrhosis caused by the B or C virus), colitis (in particular due to *Clostridium*), diarrhea (in particular bacterial diarrhea (in particular *Shigella, Campylobacter, Salmonella, Yersinia pseudotuberculosis* and *Yersinia enterocolitica*) or viral diarrhea (in particular caused by *parvovirus* and *reovirus, rotavirus* (reo-like virus), *enterovirus, astrovirus*, corona-like virus), celiac disease in adults, Whipple disease, pancreatitis, irritable bowel syndrome, abdominal tumors, liver tumors, duodenal or stomach ulcer, intestinal worms, Zollinger-Ellison syndrome.

A systemic disease is a disease located in an organ other than the gastrointestinal system.

In this embodiment, a variant of the OB-fold protein is therefore selected, in particular by means of the screening methods described in WO 2008/068637, said variant binding to a therapeutic target (etiological factor or effector) involved in the disease or the disorder that it is desired to treat, and this variant is formulated in an oral administration composition.

The invention also relates to a method for treating a systemic disease or disorder or more particularly a gastrointestinal system disease or disorder, characterized in that a composition according to the invention, containing a therapeutically effective amount of an OB-fold protein which targets (which binds to), preferably, an etiological factor or a therapeutic target characteristic of said disease or of said disorder is orally administered.

EXAMPLES

In all of the examples, nanofitins, as defined above, i.e. Sac7d variants obtained by screening a combinatorial library against a target of interest, according to a method similar to the method described in WO 2008/068637, are used. The objective of these examples is to demonstrate that the OB-fold proteins, and in particular the nanofitins, are capable of resisting degradation in the stomach and of having an effect directly on the site of the gastrointestinal system (intestine for example) where their action is required.

Example 1: Orally Administered Nanofitin Efficacy Test

Three nanofitins A1, A2, A3 resulting from screenings of a library of Sac7d variants for their affinity against a target of interest, involved in a gastrointestinal system disease (inflammation of the intestine) were tested. These nanofitins were produced in a bacterial system, either in the form of a fusion with a polyhistine tag, or in the absence of fusion (non-tagged).

The nanofitins were suspended in PBS (phosphate buffered saline).

These nanofitins were tested on a murine model of intestinal inflammation (colitis) induced with TNBS (2,4,6-trinitrobenzenesulfonic acid), as described in Scheiffele and Fuss (Curr Protoc Immunol. 2002 August; Chapter 15: Unit 15.19), either in preventive mode with the application of a dose of nanofitin per day from 5 days before induction with TNBS and sacrifice of the mice 2 days later, or in curative mode with application of a dose of nanofitin per day from the day of induction with TNBS and sacrifice of the mice 4 days later.

The effect of the nanofitins was evaluated macroscopically and histologically. For the macroscopic evaluation, the colon was examined under a dissection microscope (×5) in order to evaluate the lesions according to the Wallace criteria. The Wallace score evaluates the macroscopic lesions on a scale of 0 to 10 on the basis of criteria which reflect the inflammation (0 corresponding to the absence of inflammation and 10 to an aggravated inflammation), such as hyperemia, and the number and extent of the ulcerations (Pierre Desreumaux, 2001, J Exp Med., 193, 827-838). For the histological evaluation, a piece of colon located 2 cm above the anal canal was cut out, and then fixed overnight in 4% paraformaldehyde and embedded in paraffin. The sections stained with hematoxylin and eosin were examined "blind" and evaluated according to the Ameho criteria. The Ameho score evaluates the lesions on a scale of 0 to 6 on the basis of criteria which reflect the inflammation (0 corresponding to the absence of inflammation and 6 to an aggravated inflammation) such as cell infiltration, and the depth and extension on the surface of the lesion (Pierre Desreumaux, 2001, J Exp Med., 193, 827-838). In the two cases, the results were converted into percentage efficacy reflecting the percentage decrease in the score relative to the overall score of the non-treated induced mice.

As a control, use was made of a reference molecule sold as an intestinal anti-inflammatory, Pentasa® (5-aminosalicylic acid) used at its optimal dose. The results are indicated by way of reference more than by way of comparison, the dosages and the route of administration not being rigorously identical to those applied to the nanofitins.

When applied preventively by rectal administration (30 mM), Pentasa® gives an efficacy of 37% (macroscopic level) and 29% (histological level).

When applied in the curative model (presence ad libitum in the food of the animals), Pentasa® gives an efficacy of 59% (macroscopic level) and 39% (histological level).

TABLE I

Results obtained on intestinal inflammation model (percentage efficacy)

| | Preventive/ Curative | Dose (mg/kg) | A1 M | A1 H | A2 M | A2 H | A3 M | A3 H | A3 non-tagged M | A3 non-tagged H |
|---|---|---|---|---|---|---|---|---|---|---|
| A3 | Preventive | 10 | | | | | 27.8 | 33.6 | | |
| | | 100 | | | | | 18.2 | 28.1 | | |
| | | 400 | | | | | 48.6 | 45.1 | | |
| A3 non-tagged | Preventive | 10 | | | | | | | 32 | 26 |
| | | 100 | | | | | | | 65 | 75 |
| | | 400 | | | | | | 54 | 61 | 56 | 70 |
| Efficacy in curative model | Curative | 100 | 32 | 43 | 26 | 30 | 37 | 43 | | |

M: Efficacy at the macroscopic level
H: Efficacy at the histological level

These results show that the nanofitins are capable of acting directly on the target located in the intestine after oral administration, that they effectively pass through the stomach without being degraded, and that they exhibit efficacy levels comparable with the reference product.

The invention claimed is:

1. An oral administration composition comprising a variant of a wild-type OB-fold protein, said variant having between 5 and 32 mutated residues in the interface of binding of said wild-type OB-fold protein to its natural ligand.

2. The composition as claimed in claim 1, characterized in that said wild-type OB-fold protein is selected from the group consisting of Sac7d or Sac7e derived from *Sulfolobus acidocaldarius*, Sso7d derived from *Sulfolobus solfataricus*, DBP 7 derived from *Sulfolobus tokodaii*, Ssh7b derived from *Sulfolobus shibatae*, Ssh7a derived from *Sulfolobus shibatae*, and p7ss derived from *Sulfolobus solfataricus*.

3. The composition as claimed in claim 1, characterized in that said variant binds to a target of interest selected from the group consisting of antigens, antibodies, cell proteins, circulating proteins, peptides, active ingredients of medicaments, nucleic acids, interleukins, cytokines, cytokine or interleukin receptors, proteins encoded by oncogenes, surface proteins of microorganisms, and microorganism lipopolysaccharides.

4. The composition as claimed in claim 1, characterized in that it is in the form of gel capsules, tablets, lozenges or pills.

5. The composition as claimed in claim 1, characterized in that it is in the form of a liquid composition.

6. The composition as claimed in claim 1, characterized in that it also comprises at least one agent selected from the group consisting of an antibacterial, an antiparasitic, an antifungal, an anti-inflammatory, an antipruritic, an anesthetic, an antiviral, a keratolytic and a free-radical-scavenger agent.

7. A process for preparing an oral administration composition as claimed in claim 1, comprising the step of mixing a variant of a wild-type OB-fold protein, said variant having between 5 and 32 mutated residues in the interface of binding of said wild-type OB-fold protein to its natural ligand with a pharmaceutically acceptable oral administration carrier.

8. A process for detecting the presence of a specific antigen in an organ, comprising the step of administering to said patient a composition as claimed in claim 1, said composition comprising a variant of an OB-fold protein which binds to said desired antigen, and which is coupled to a tracer.

9. A process of claim 8, wherein the organ is the gastrointestinal system.

10. The composition as claimed in claim 2, characterized in that said variant binds to a target of interest selected from the group consisting of antigens, antibodies, cell proteins, circulating proteins, peptides, active ingredients of medicaments, nucleic acids, interleukins, cytokines, cytokine or interleukin receptors, proteins encoded by oncogenes, surface proteins of microorganisms, and microorganism lipopolysaccharides.

11. The composition as claimed in claim 2, characterized in that it is in the form of gel, capsules, tablets, lozenges or pills.

12. The composition as claimed in claim 2, characterized in that it is in the form of a liquid composition.

13. The composition as claimed in claim 2, characterized in that it also comprises at least one agent selected from the group consisting of an antibacterial, an antiparasitic, an antifungal, an anti-inflammatory, an antipruritic, an anesthetic, an antiviral, a keratolytic and a free-radical-scavenger agent.

14. The composition as claimed in claim 3, characterized in that it also comprises at least one agent selected from the group consisting of an antibacterial, an antiparasitic, an antifungal, an anti-inflammatory, an antipruritic, an anesthetic, an antiviral, a keratolytic and a free-radical-scavenger agent.

15. A method for administering a variant of a wild-type OB-fold protein, said variant having between 5 and 32 mutated residues in the interface of binding of said wild-type OB-fold protein to its natural ligand comprising the step of orally administering the oral administration composition of claim 1, wherein said wild-type OB-fold protein is selected from the group consisting of Sac7d or Sac7e derived from *Sulfolobus acidocaldarius*, Sso7d derived from *Sulfolobus solfataricus*, DBP 7 derived from *Sulfolobus tokodaii*, Ssh7b derived from *Sulfolobus shibatae*, Ssh7a derived from *Sulfolobus shibatae*, and p7ss derived from *Sulfolobus solfataricus*.

16. The method of claim 15, wherein administration of said variant treats a gastrointestinal system disorder in said patient.

17. The method of claim 15, wherein said variant binds to a target of interest selected from the group consisting of antigens, antibodies, cell proteins, circulating proteins, peptides, active ingredients of medicaments, nucleic acids, interleukins, cytokines, cytokine or interleukin receptors, proteins encoded by oncogenes, surface proteins of microorganisms, and microorganism lipopolysaccharides.

18. The method of claim 15, wherein the composition is in the form of gel capsules, tablets, lozenges or pills.

19. The method of claim 15, wherein the composition is in the form of a liquid composition.

20. The method of claim 15, wherein the composition also comprises at least one agent selected from the group consisting of an antibacterial, an antiparasitic, an antifungal, an anti-inflammatory, an antipruritic, an anesthetic, an antiviral, a keratolytic and a free-radical-scavenger agent.

21. The method of claim 15, whereby a pharmacologically effective amount of the variant is delivered to the intestine and/or crosses the barrier of the intestine.

* * * * *